US005759842A

United States Patent [19]
Dombrowski et al.

[11] Patent Number: 5,759,842
[45] Date of Patent: Jun. 2, 1998

[54] IN VITRO HIV INTEGRASE INHIBITORS

[75] Inventors: Anne W. Dombrowski, East Brunswick, N.J.; Jeffrey C. Hastings, Erdenheim; Daria Jean Hazuda, Lansdale, both of Pa.; Jon David Polishook, Cranford; Sheo Bux Singh, Edison, both of N.J.

[73] Assignee: Merck & Co., Inc., Rahway, N.J.

[21] Appl. No.: 736,092

[22] Filed: Oct. 24, 1996

[51] Int. Cl.$^6$ .............. C12N 1/12; C12N 1/00; C12P 17/10; C07D 707/00
[52] U.S. Cl. .............. 435/252.1; 435/121; 435/911; 548/539
[58] Field of Search .............. 435/252.1, 121, 435/911; 548/539

[56] References Cited

U.S. PATENT DOCUMENTS 5,352,800  10/1994  Bills et al. .............. 548/539

FOREIGN PATENT DOCUMENTS

WO 96/28443  9/1996  WIPO.

OTHER PUBLICATIONS

LaFemina et al., Antimicrobial Agents & Chemotherapy, vol. 39(2), pp. 320–324 (1995), "Inhibition of human immunodeficiency virus integrase by bis–catechols".

Cushman et al., J. Med. Chem., vol. 38 (1995), pp. 443–452, "Cosalane analogues with enhanced potencies as inhibitors of HIV–1 protease and integrase".

Mazumder et al., Biochemistry, vol. 34 (1995), pp. 15111–15122, "Effects of tyrphostins, protein kinase inhibitors, on human immunodeficiency virus type 1 integrase".

Mazumder et al., J. Med. Chem., vol. 39 (1996), pp. 2472–2481, "Antiretroviral agents as inhibitors of both human immunodeficiency virus type 1 integrase and protease".

Mazumder et al., Molecular Pharmacology, vol. 49 (1996), pp. 621–628, "Effects of nucleotide analogues on human immunodeficiency virus type 1 integrase".

Kusumoto et al., C.A. 120(19):238888s, "A comparative study on the inhibitory effects of flavonoids and alkaloids on reverse transcriptases of different retroviruses".

Mazumder et al., AIDS Research and Human Retroviruses, vol. 11(1), pp. 115–125 (1995), "Inhibition of human immunodeficiency virus type 1 integrase by a hydrophobic cation . . .".

Mazumder et al., Proc. Nat'l Acad. Sci. USA, vol. 91, pp. 5771–5775 (1994), "Inhibition of human immunodeficiency virus type 1 integrase by 3'–azido–3'–deoxythymidylate".

Carteau et al., Biochemical Pharm., vol. 47(10), pp. 1821–1826 (1994), "Inhibition of the in vitro integration of moloney murine leukemia virus DNA by the DNA minor groove binder netropsin".

Fesen et al., Proc. Nat'l Acad. Sci. USA, vol. 90 (1993), pp. 2399–2403, "Inhibitors of human immunodeficiency virus integrase".

Farnet et al., Proc. Nat'l Acad. Sci. USA, vol. 93 (1996), pp. 9742–9747, "Differential inhibition of HIV–1 preintegration complexes and purified integrase protein by small molecules".

Lutzke et al., Proc. Nat'l Acad. Sci. USA, vol. 92 (1995), pp. 11456–11460, "Identification of a hexapeptide inhibitor of the human immunodeficiency virus integrase protein by using a combinatorial chemical library".

Ojwang et al., Antimicrobial Agents & Chemotherapy, vol. 39(11), pp. 2426–2435 (1995), "T30177, an oligonucleotide stabilized by an intramolecular guanosine octet, is a potent inhibitor . . .".

Eich et al., J. Med. Chem., vol. 39 (1996), pp. 86–95, "(–)–Arctigenin as a lead structure for inhibitors of human immunodeficiency virus type–1 integrase".

Konig et al., J. of Bioenergetics & Biomembranes, vol. 25(5), pp. 537–545 (1993), "Effects of equisetin on rat liver mitochondria: evidence for inhibition of substrate anion carriers of the inner membrane".

Philipps et al., J. Am. Chem. Soc., vol. 111 (1989), pp. 8223–8231, "Characterization of the fusarium toxin equisetin: the use of phenylboronates in structure assignment".

Turos et al., J. Am. Chem. Soc., vol. 111 (1989), pp. 8231–8236, "Total synthesis of the fusarium toxin equisetin: proof of the stereochemical relationship of the tetramate and terpenoid sectors".

Hazuda et al., Nucleic Acids Research, vol. 22(6), pp. 1121–1122 (1994), "A novel assay for the DNA strand–transfer reaction of HIV–1 integrase".

Burke et al., J. Med. Chem., vol. 38 (1995), pp. 4171–4178, "Hydroxylated aromatic inhibitors of HIV–1 integrase".

Hazuda et al., J. of Virology, vol. 71(1), pp.807–811 (1997), "Equivalent inhibition of half-site and full–site retroviral strand transfer reactions by structurally diverse compounds".

Fesen et al., Biochemical Pharma., vol. 48(3), pp. 595–608 (1994), "Inhibition of HIV–1 integrase by flavones, caffeic acid phenthyl ester (cape) and related compounds".

Carteau et al., Archives of Biochemistry & Biophysics, vol. 305(2), pp. 606–610 (1993), "Inhibitory effect of the polyanionic drug suramin on the in vitro HIV DNA integration reaction".

Robinson, Jr., et al., Proc. Nat'l Acad. Sci. USA, vol. 93 (1996), pp. 6326–6331, "Inhibitors of HIV–1 replication that inhibit HIV integrase".

PRNewswire, Sep. 17, 1996, "Aronex reports results for lead anti–HIV integrase inhibitor compound".

*Primary Examiner*—Marian C. Knode
*Assistant Examiner*—Ali Salimi
*Attorney, Agent, or Firm*—Catherine D. Fitch; William H. Nicholson

[57] ABSTRACT

Natural products such as equisetin and derivatives are described. These compounds are useful in the inhibition of HIV integrase.

4 Claims, No Drawings

IN VITRO HIV INTEGRASE INHIBITORS

CROSS-REFERENCE TO RELATED APPLICATIONS

This application claims priority of Ser. No. 60/005,906, filed Oct. 27, 1995, now abandoned.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid cells. Integration is believed to occur in three stages: cleavage of two nucleotides from the 3' termini of the linear proviral DNA; covalent joining of the recessed 3' OH termini of the proviral DNA at a staggered cut made at the host target site; repair synthesis by host enzymes.

Nucleotide sequencing of HIV shows the presence of a pol gene in one open reading frame [Ratner, L. et al., Nature, 313, 227 (1985)]. Amino acid sequence homology provides evidence that the pol sequence encodes reverse transcriptase, an integrase and an HIV protease [Toh, H. et al., EMBO J. 4, 1267 (1985). Power, M. D. et al., Science, 231, 1567 (1986); Pearl, L. H. et al., Nature 329, 351 (1987)].

It is known that some antiviral compounds act as inhibitors of HIV and are effective agents in the treatment of HIV and similar diseases, e.g., azidothymidine or AZT. Applicants demonstrate that the compounds of this invention are inhibitors of HIV integrase, probably by inhibiting strand transfer and cleavage activity. The particular advantage of the present invention is specific inhibition of HIV integrase.

One compound of the present invention, Equisetin, has been previously isolated from *Fusarium equiseti* by Lynn et al. (J. Am. Chem. Soc., 111, 8223, 1989) and subsequently synthesized by Danishefsky, et al. (J. Am. Chem. Soc., 111, 8231, 1989). Equisetin is known to inhibit DNP-stimulated ATPase activity of rat liver mitochondria and mitoplast $IC_{50} \sim 8$ nM (Koenig et al., J. Bioenerg. Biomembr., 25, 537–545, 1993). Equisetin possesses two distinct structural moieties: the upper tetramic acid type polar component and the lower hydrophobic sesquiterpene component.

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

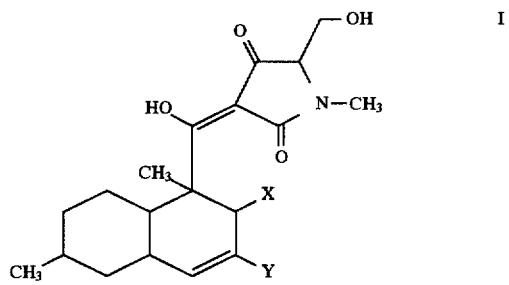

wherein X is

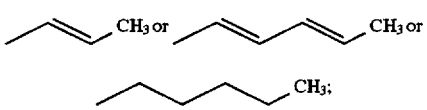

Y is H or $CH_3$, or pharmaceutically acceptable salts thereof, with the proviso that the compound is not

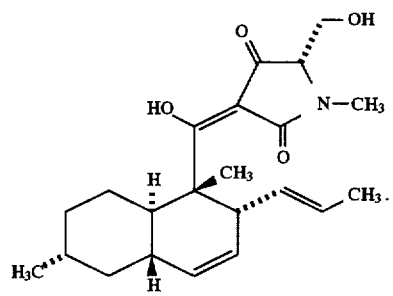

One preferred embodiment of the present invention is a compound of the formula

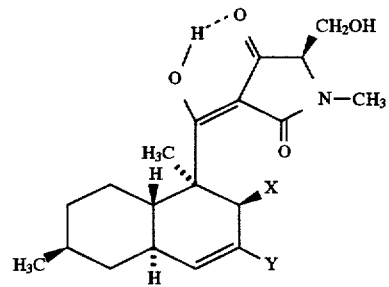

wherein X is

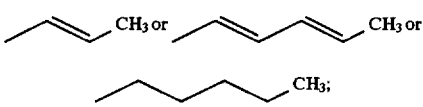

Y is H or $CH_3$, or pharmaceutically acceptable salts thereof.

One preferred compound of the present invention is equisetin, which is useful for inhibiting HIV integrase. Equisetin has the structure Compound A:

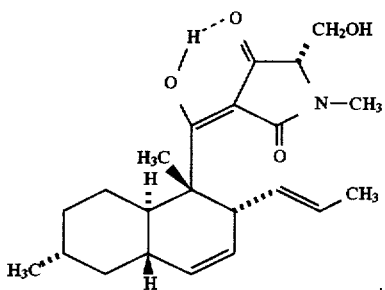

Another preferred compound of this invention follows:

Compound B:

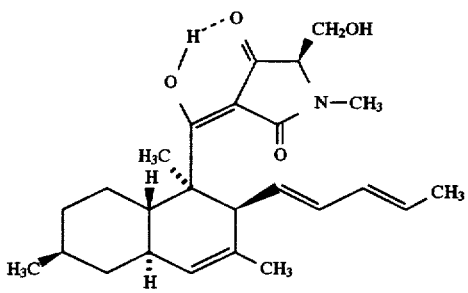

or pharmaceutically acceptable salt(s) thereof.
Another preferred compound follows:

Compound C:

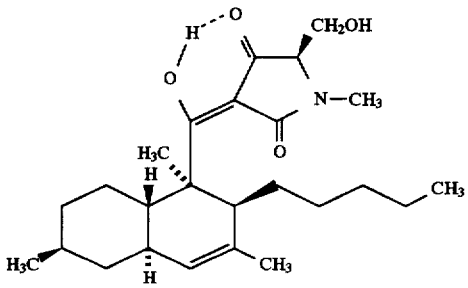

or pharmaceutically acceptable salt(s) thereof:

Also covered by the present invention are pharmaceutical compositions useful for inhibiting HIV integrase, comprising an effective amount of a compound of this invention. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. This invention also discloses the cultures MF6069 and MF6070.

The compounds of the present invention may have asymmetric centers and may occur, except when specifically noted, as mixtures of stereoisomers or as individual diastereomers, or enantiomers, with all isomeric forms being included in the present invention.

When any variable (e.g., X, Y, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

Applicants have discovered that equisetin, recovered from a culture of the fungus Fusarium heterosporum (MF6069), is useful for inhibiting HIV integrase. Applicants have also discovered that compounds related to equisetin, recovered from a culture of the fungus Phoma sp. (MF6070), are also useful for inhibiting HIV integrase.

ATCC Deposit 74349

Before the U.S. filing date of the present application, a sample of the fungus Fusarium heterosporum sp. (MF6069) had been deposited at the American Type Culture Collection (ATCC), 12301 Parklawn Drive, Rockville, Md. 20852. The culture access designation is 74349. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

ATCC Deposit 74348

Before the U.S. filing date of the present application, a sample of the fungus Phoma sp. (MF6070) has been deposited at the American Type Culture Collection (ATCC), 12301 Parklawn Drive, Rockville, Md. 20852. The culture access designation is 74348. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics of ATCC 74349 (MF6069)

MF6069 is the fungus Fusarium heterosporum Nees (Hyphomycetes, Deuteromycotina). The key taxonomic characteristics of this species include dorsiventral macroconidia which vary in size and are 1–5 septate, a peach to orange colored mycelium in culture, and the absence of microconidia and chlamydospores (Booth, C., The Genus Fusarium, Commonwealth Mycological Institute, Kew, Surrey, England, 1971). F. heterosporum is known to be the anamorph of the ascomycete Gibberella gordonia C. Booth. However, this sexual state is not being produced under the cultural conditions described in this application. MF6069 was isolated from a plant material from Costa Rica.

Description of Fusarium heterosporum Nees

MF6069 was isolated according to the method of Bills, G. F. and Polishook, J. D., Mycologia, 86, 187 (1994) from leaf litter from *Rehdera trinervis* (Verbenaceae), collected in the Area de Conservacion Guanacaste, Parque National Santa Rosa, Provincia de Guanacaste, Costa Rica. In the following description, all capitalized color names are from Ridgway, R., Color Standards and Color Nomenclature. Publ. by the author, Washington, D.C. (1912). All observations made on colonies grown for 7 days at 25° C. and 67% relative humidity in 12 hr. photoperiod.

On oatmeal agar colony attains a diameter of 85 mm. Colony mat white, woolly, growing to the top of the petri dish lid; colony mat center slightly depressed, yellowish; reverse, soluble pigment and exudate absent.

On potato-dextrose agar colony attains a diameter of 65 mm. Colony mat woolly, mostly near margin, cottony at the center, light orange (Orange-Pink, Safrano Pink) and light yellow (Pale Orange-Yellow); margin white, cottony, dissected; reverse orange (Bittersweet Pink, Light Salmon-Orange); soluble pigment and exudate absent.

On MYE (1% malt extract, 0.2% yeast extract) colony attains a diameter of 85 mm. Colony mat white, woolly, some sections to the top the lid, some sections pinkish (Orient Pink); margin white, cottony, not entire; reverse pinkish (Light Salmon-Orange); soluble pigment or exudate absent; at 37° C. and in the dark, colony attaining a diameter of 12 mm after 7d; culture mat cottony, orange (Mikado Orange); margin white, cottony; reverse, soluble pigment and exudate absent.

On cornmeal agar colony attains a diameter of 85 mm. Colony mat hyaline, appressed with sparse cottony tufts throughout and hyaline sporodochia; margin hyaline, entire; reverse, soluble pigment and exudate absent.

Sporodochia discrete, becoming pionnote after 5–7 days. Conidiophores densely branched, forming whorls of 1–3 phialides, 7–12 ×2–3 µm. Macroconidia variable in size, dorsiventral with a pedicillate basel cell and an elongated apical cell with a slight beak, 1–5 septate, 25–40×3–4 µm. Microconidia and chlamydospores absent.

General Characteristics of ATCC 74348 (MF6070)

MF6070 is placed in the fungal genus Phoma (Coelomycetes, Deuteromycotina). The key taxonomic characteristics of this genus include pycnidial conidiomata, enteroblastic, ampuliform conidiogenous cells, conidia that are hyaline, elliptical, guttulate and exuded in a mucoid mass, according to Sutton, B., The Coelomycetes. Commonwealth Mycological Institute, Kew, Surrey, England (1980).

MF6070 was isolated from soil collected in a karstic dry pool from Clot Déspola, near Banyolas (Province of Gerona), Spain. In the following description, all capitalized color names are from Ridgway, (1912) supra. All observations made on colonies grown for 7 days at 25° C. and 67% relative humidity in 12 hr. photoperiod.

On oatmeal agar colony attains a diameter of 30 mm. Colony mat cottony, mounded up from margin to center, gray (Puritan Gray, Light Mineral Gray), sulcate; margin hyaline, entire; reverse a faint green; soluble pigment and exudate absent.

On potato-dextrose agar colony attains a diameter of 24 mm. Colony mat cottony, gray-green (Light Olive-Gray, Olive-Gray), sulcate; margin entire, faint brown; reverse dark drown (Saccardo's Umber, Olive Brown); soluble pigment and exudate absent.

On MYE (1% malt extract, 0.2% yeast extract) colony attains a diameter of 19 mm. Colony mat cottony, gray (Smoke Gray, Pale Smoke Gray); margin white,. entire; reverse, soluble pigment and exudate absent; at 37° C. and in the dark, no growth.

On cornmeal agar colony attains a diameter of 20 mm. Colony mat hyaline appressed with sparse cottony tufts near the margin; margin hyaline, entire; reverse, soluble pigment and exudate absent.

Conidiomata pycnidial, olivaceous to black, 100–300 µm in diameter, globose to subglobose, sometimes irregular shaped with many ostioles, usually covered by a loose network of mycelium. Conidiogenous cells ampulliform, phialidic. Conidial exudate cream colored. Conidia predominately elliptical to cylindrical, smooth-walled, hyaline, biguttulate, 4–5×1–2 µm.

In General, ATCC 74349 strain or ATCC 74348 strain are cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH of about 6–8 at the initiation and termination (harvest) of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, dextrin, and the like. Other cources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions is one method of culturing the cells. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 6–7 to the autoclaving step.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably 22°–25° C., for a period of about 14–21 days, which may be varied according to fermentation conditions and scales.

Preferred culturing/production media for carrying out the fermentation include Medium A and Medium B as set forth in the Examples.

After growth is completed, the cells are harvested by conventional methods, e.g., centrifugation and filtration, and then extracted with the appropriate solvent, e.g., methylethylketone.

The product equisetin and derivatives can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate was separated and concentrated to dryness initially by evaporating under reduced pressure followed by lyophilization. The compounds were finally isolated wither by solvent partitioning and crystallization or by preparative HPLC on reversed phase systems.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1.3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally admintered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/g body weight in divided doses. One preferred dosage range is 0.1 to 100 mg/g body weight orally in divided doses. Another preferred dosage range is 0.1 to 200 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the hose undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
| --- | --- | --- |
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |

-continued

| Drug | Manufacturer | Indication |
|---|---|---|
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant interferon in an immuno-adsorption column | Advanced Biotherapy Concepts (Rockville, MD) | AIDS, ARC |
| MK-639 | Merck (Rahway, NJ) | AIDS, ARC, asymptomatic HIV positive, also in combination with AZT. |

IMMUNO-MODULATORS

| Drug | Manufacturer | Indication |
|---|---|---|
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoechst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposit's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposit's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposits sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |

ANTI-INFECTIVES

| Drug | Manufacturer | Indication |
|---|---|---|
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |

OTHER

| Drug | Manufacturer | Indication |
|---|---|---|
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. |

| Total Enteral Nutrition | Norwich Eaton Pharmaceuticals (Norwich, NY) | w/AIDS diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

The compound MK-639 is an inhibitor of HIV protease and is N-(2(R)-hydroxy-1(S)-indanyl)-2(R)-phenylmethyl-4-(S)-hydroxy-5-(1 -(4-(3-pyridyl-methyl)-2(S)-N'-(t-butylcarboxamido)-piperazinyl))-pentaneamide, or pharmaceutically acceptable salt thereof, and is synthesized according to U.S. Pat. No. 5,413,999.

EXAMPLE 1

Fermentation

A. Culture:

MF6069 and MF6070 were used to prepare FVMs (frozen vegetative mycelia). A portion of the agar slant was transferred aseptically to seed medium. (The composition of the seed medium is detailed in Table 1).

TABLE 1

Composition of Seed and Production Media
SEED MEDIUM

| Component | g/L |
|---|---|
| Yeast extract | 4.0 |
| Malt extract | 8.0 |
| Glucose | 4.0 |
| Polyanionic polyacrylic acid | 1.5 |

The medium was prepared with distilled water, the pH adjusted to 7.0 prior to sterilization and was dispensed at 50 ml/250ml unbaffled flask. Cotton closures were used. Sterilization was at 121° C. for 20 minutes.

The flasks were incubated on a 2-inch throw gyratory shaker, 220 rpm for 2 days at 25° C., 85% relative humidity (rh), to obtain biomass. Portions of the biomass were transferred into sterile vials containing glycerol and frozen (as FVM). These were maintained in a final concentration of 10–15% glycerol at −75° C.

B. Seed:

Frozen vials (FVM) were thawed to room temperature and used to inoculate seed cultures, at 1.0 ml per 50 ml seed medium. The cultures were grown on a gyratory shaker (220 rpm) for 2-3 days at 25° C., 85% rh, until a sufficient amount of biomass was obtained.

C. Production:

The composition of the solid substrate fermentation media are shown below. An aliquot (12 ml) of each grown seed was placed into 220 ml of the liquid portion of the production media (Medium A for MF6069 and Medium B for MF6070). Each production culture was swirled vigorously to disperse the biomass. The contents were dispensed by pouring into a 2-liter roller culture vessel which contained 675 cubic centimeters of steam-sterilized large-particle vermiculite. The contents of the roller bottle were shaken/mixed to insure homogeneous inoculation and coverage. The roller bottles were incubated horizontally, revolving at approximately 4 rpm on a roller apparatus, at 22° C., 75% rh for 18–19 days, to obtain secondary metabolite production in the fermentation medium.

Medium A and Medium B are defined as follows:

PRODUCTION MEDIA

Medium A
1. Solid portion:
Add 675 cc vermiculite to a 2-liter roller bottle. Plug with latex closure; autoclave for 60 minutes, plus 30 minutes dry.
2. Liquid Portion:

| Component | g/L |
|---|---|
| Glucose | 50.0 |
| NZ amine Type A | 4.0 |
| Urea | 4.0 |
| $K_2HPO_4$ | 0.5 |
| KCl | 0.25 |
| $MgSO_4 \cdot 7H_2O$ | 0.25 |
| $ZnSO_4 \cdot 7H_2O$ | 0.9 |
| $CaCO_3$ | 16.5 |

The medium was prepared with distilled water (no pH adjustment), dispensed at 220 ml in 500 ml bottles, and sterilized at 121° C. for 15 minutes.

Medium B
1. Solid portion:
Add 675 cc vermiculite to a 2-liter roller bottle. Plug with latex closure; autoclave for 60 minutes, plus 30 minutes dry.
2. Liquid Portion:

| Component | g/L |
|---|---|
| Glucose | 150.0 |
| Glycerol | 20.0 |
| Yeast Extract | 4.0 |
| $NaNO_3$ | 1.0 |
| Sodium Glutamate | 3.0 |
| $Na_2HPO_4$ | 0.5 |
| $MgSO_4 \cdot 7H_2O$ | 1.0 |
| K-elements | 1.0ml/L |
| $CaCO_3$ | 8.0 |

The medium was prepared with distilled water (pH to 7.0 before adding $CaCO_3$), dispensed at 220 ml in 500 ml bottles, and sterilized at 121° C. for 15 minutes.

| K-elements | |
|---|---|
| Component | g/L |
| $FeCl_3 \cdot 6H_2O$ | 5.8 |
| $MnSO_4 \cdot H_2O$ | 0.1 |
| $CoCl_2 \cdot 6H_2O$ | 0.02 |
| $CuSO_4 \cdot 5H_2O$ | 0.015 |
| $Na_2MoO_4 \cdot 2H_2O$ | 0.012 |
| $ZnCl_2$ | 0.02 |
| $SnCl_2 \cdot 2H_2O$ | 0.005 |
| $H_3BO_3$ | 0.01 |
| KCl | 0.02 |
| HCl (concentrated) | 2.0 ml/L |

EXAMPLE 2

Identification of HIV Integrase Inhibitor A as Equisetin

Bioassay-guided Isolation: Fifty mL fermentation broth of *Fusarium heterosporum* (MF6069; ATCC 74349) was extracted with 50 mL of methyl ethyl ketone (MEK). MEK extract, which possessed all HIV-integrase activity, was concentrated to dryness under reduced pressure followed by lyophilization to give 50 mg of a brown powder. The material was suspended in 10 mL methanol and centrifugated. The supernatant was chromatographed on a neutral polysaccharide based LH-20 column (1 L) which was eluted with methanol. The integrase activity was eluted between 400–450 mL of elution volume. The active fractions were combined and chromatographed on a reverse-phase C-8 silica gel (20×250 mm) HPLC column and eluted, at a flow rate of 10 mL per min, initially at 30% aqueous acetonitrile (containing 0.1% TFA) for 6 minutes followed by a linear gradient of 30% to 80% of aqueous acetonitrile (containg 0.1% TFA) over 40 min. All of the integrase activity was concentrated in a single peak eluting between 47–48 min. The combined active fractions were concentrated under reduced pressure and then lyophilized to give equisetin (17 mg) as a colorless powder. The compound was homogeneous by analytical HPLC, reverse-phase C-8 silica gel, 80% aqueous acetonitrile +0.1% TFA; flow rate 1 mL/min; $t_R$ 6.4 min) and by NMR. $[\alpha]D^{25}$ −384° (c, 0.39, CHCl$_3$).

Follow-up Isolation: Three liters fermentation broth of *Fusarium heterosporum* was extracted twice with three liters each of methyl ethyl ketone and the extract was concentrated to dryness using a rotatory evaporator under reduced pressure. Removal of the residual water by lyophilization gave an oily residue weighing 3.2g. The oily material was dissolved in methanol (100 mL) and was diluted with 200 mL of water. The aqueous methanolic solution was sequentially partitioned with hexane (2×300 mL) and ethyl acetate (2×300 mL). Most of the equisetin was concentrated in hexane extract with oily material. The ethyl acetate extract contained equisetin without oily residue. The hexane extract was further extracted with methanol (2×200 mL). The methanol extract possessed almost all of equisetin and the oily residue remained hexane soluble. The methanol extract was concentrated under reduced pressure to yield 1.5 g of a gum. Both methanol and ethyl acetate extracts were combined to give a total 1.9 g of the crude material. A portion of this material was purified on a preparative reverse-phase C-8 silica gel (20×250 mm) HPLC column using a sequential gradient at a flow rate of 10 mL per min. Initially, the column was eluted with 30% aqueous acetonitrile (+0.1% TFA) for seven min followed by a linear gradient to 70% over 60 min, holding at 70% for 10 min followed by a 10 min gradient to 80% aqueous acetonitrile. Equisetin was eluted between 70–71 min. This procedure was very reproducible and 200 mg of the crude material could easily be injected.

Search of the C-13 NMR data base gave equisetin as the best match. This was confirmed with the comparison of the published C-13 shifts of equisetin with that of Compound A (Table 2). Further corroboration of the identity of A with that of equisetin came from comparison of their UV, $^1$H-NMR spectra, MS fragmentation and optical rotation.

TABLE 2

Table: C-13 NMR Compound A in Comparison with Equisetin in CDCl$_3$ at 300 MHz.

| Position | Type | Equisetin | Compound A |
|---|---|---|---|
| 1 | C° | 190.6 | 190.6 |
| 2 | C° | 48.4 | 48.5 |
| 3 | CH | 44.6 | 44.5 |
| 4 | CH | 127.1* | 127.1 |
| 5 | CH | 130.4** | 130.9 |
| 6 | CH | 38.4 | 38.6 |
| 7 | CH$_2$ | 41.9 | 42.2 |

TABLE 2-continued

Table: C-13 NMR Compound A in Comparison with Equisetin in CDCl$_3$ at 300 MHz.

| 8 | CH$_2$ | 33.3 | 33.5 |
|---|---|---|---|
| 9 | CH$_2$ | 35.5 | 35.7 |
| 10 | CH$_2$ | 28.1 | 28.3 |
| 11 | CH | 39.6 | 39.7 |
| 12 | CH$_3$ | 13.7 | 13.8 |
| 13 | CH | 129.8** | 130.1 |
| 14 | CH | 126.2* | 126.6 |
| 15 | CH$_3$ | 18.2 | 18.0 |
| 16 | CH$_3$ | 22.5 | 22.5 |
| 2' | C° | 176.7 | 177.0 |
| 3' | C° | 99.8 | 99.5 |
| 4' | C° | 198.9 | 199.5 |
| 5' | CH$_2$ | 66.4 | 66.7 |
| 6' | CH | 60.0 | 60.5 |
| 7' | CH$_3$ | 27.2 | 27.4 |

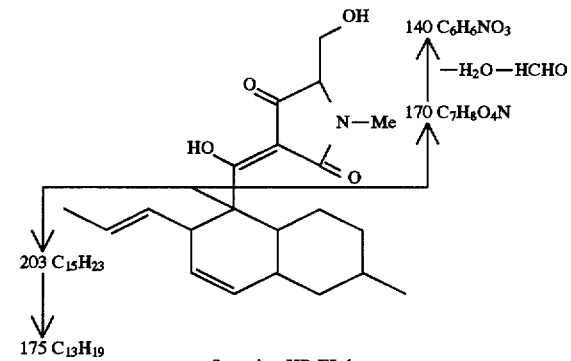

Scanning HR-EI data

| Observed m/z | Int % | Composition |
|---|---|---|
| 373.2254 | 47.9 | C22H31O4N |
| 355.2131 | 36.1 | C22H29O3N |
| 210.0748 | 60.6 | C10H12O4N |
| 203.1774 | 42.7 | C15H23 |
| 199.0826 | 90.4 | C9H13O4N |
| 183.0840 | 26.9 | C9H13O3N |
| 175.1453 | 34.8 | C13H19 |
| 170.0466 | 100.0 | C7H8O4N |

EXAMPLE 3

Characterization of Compound B

Bioassay-guided Isolation: One hundred mL of fermentation broth of Phoma sps. (MF6070, ATCC 74348) was extracted with 100 mL of methyl ethyl ketone (MEK). MEK extract, which showed HIV-integrase activity, was concentrated to dryness under reduced pressure followed by lyophilization to give 100 mg of a brown gum. This material was dissolved in methanol (20 mL), acetone (20 mL) and methylene chloride (10 mL). The soluble portion was chromatographed on a one liter neutral polysaccharide bases LH-20 column. The column was eluted with methanol and the integrase active fractions, which eluted between 400–500 mL of elution volume, were combined. The combined fractions were chromatographed on a reverse-phase C-8 silica gel (20×250 mm) HPLC column and eluted at a flow rate of 10 mL per min using a linear gradient of 30% to 80% of aqueous acetonitrile (containg 0. I% TFA) over 40 min, holding at 80% aqueous acetonitrile for 15 minutes followed by a 10 min gradient to 100% acetonitrile. Most of the integrase activity was concentrated in a single peak eluting at 47–48 min. The fractions containing the activity were concentrated under reduced pressure and then lyophilized to give colorless powder of Compound B (9 mg).

Follow-up Isolation: Two liters fermentation broth of Phoma sps. was extracted twice with two liters each of methyl ethyl ketone and the extract was concentrated to dryness using a rotatory evaporator under reduced pressure. Removal of the residual water by lyophilization gave an oily residue weighing 4.6 g. The oily material was dissolved in methanol (100 mL) and was diluted with 200 mL of water. The aqueous methanolic solution was sequentially partitioned with hexane (2×300 mL) and ethyl acetate (2×300 mL). Ethyl acetate extract contained almost exclusively Compound B, though traces of Compound B was also present in hexane extract and aqueous methanolic layer. The ethyl actate extract was dried over sodium sulphate and concentrated under reduced pressure to 800 mg of highly enriched Compound B as a powder.

The powdery material obtained from ethyl acetate extract was dissolved in acetone (10 mL) and methylene chloride (10 mL) and filtered. The filtrate was concentrated to dryness and was crystallized from 20 mL hot benzene to give Compound B as a colorless powder (175 mg). Additional amounts of Compound B was obtained from the mother liquor by chromatography on HPLC using a neutral reverse-phase silica gel column as described below.

The mother liquor was concentrated to dryness and was dissolved in methanol (3.4 mL). Half (1.7 mL) of the methanolic solution was chromatographed on a reverse-phase C-8 silica gel (20×250 mm) HPLC column and eluted, at 10 mL per min, with a linear gradient of 40% to 80% aqueous acetonitrile (containing 0.1% trifluroacetic acid) over a period of 60 minutes and holding at 80% aqueous acetonitrile for 20 min. Compound B was eluted between 55–60 min. Repetition of the chromatographic separation with the remainder of the material followed by lyophilization of the combined fractions afforded Compound B (120 mg) as a amorphous powder. The compound was homogeneous by analytical HPLC, reverse-phase C-8 silica gel, 4.6×250mm, 80% aqueous acetonitrile +0.1% TFA; flow rate 1 mL/min; $t_R$ 8.5 min) and by NMR.

Mass spectral analysis of the active compound gave a MW of 413 and a MF of $C_{25}H_{35}NO_4$. This formula has an additional $C_3H_4$ unit compared to equisetin. Mass spectral fragment ion m/z 170 is the same as that observed with equisetin. Equisetin based substructure search in all data bases did not give any possible match indicating this compound may be novel.

| Scanning HR-EI Data | | |
|---|---|---|
| Observed m/z | Int % | Composition |
| 413.2565 | 100.0 | C25H35O4N |
| 398.2334 | 8.8 | C24H32O4N |
| 395.2483 | 11.2 | C25H33O3N |
| 243.2044 | 50.0 | C18H27 |
| 225.1007 | 59.0 | C11H15O4N |
| 189.1614 | 44.4 | C14H21 |
| 170.0472 | 59.5 | C7H8O4N |
| 143.0679 | 17.9 | C6H9O3N |
| 140.0386 | 38.1 | C6H6O3N |
| 119.0846 | 31.5 | C9H11 |
| 105.0705 | 26.3 | C8H9 |

The structure of Compound B was elucidated by extensive use of NMR using $CD_3CN$ as a solvent. The relative stereochemistry was determined by a NOESY experiment and found to be identical to that of equisetin. The data is summarized below.

TABLE

NMR assignments of Compound B in $CD_3CN$ at 25° C.

| Position | δC | multi (APT) | δH | HMBC (C→H) |
|---|---|---|---|---|
| 1 | 197.52 | C° | — | H-12 |
| 2 | 49.90 | C° | — | H-3,H-12 |
| 3 | 50.22 | CH | 3.17,brd,9 | H-5,H-12,H-14,H-18 |
| 4 | 132.45 | C° | — | H-3,H-6,H-18 |
| 5 | 127.08 | CH | 5.22,brs | H-3,H-6,H-18 |
| 6 | 40.07 | CH | 1.84,m | H-5 |
| 7 | 43.14 | CH₂ | 1.78,m 0.85,appq,12 | H-5,H-6,H-19 |
| 8 | 34.28 | CH | 1.50,m | H-6,H-7,H-19 |
| 9 | 36.59 | CH₂ | 1.74,m 1.04,m | H-19 |
| 10 | 28.97 | CH₂ | 1.96,m 1.05,m | H-6 |
| 11 | 40.55 | CH | 1.62,m | H-3,H-5,H-6,H-7,H-12 |
| 12 | 14.23 | CH₃ | 1.68,brs | H-3 |
| 13 | 131.59 | CH | 5.25,dd,12,10 | H-3,H-15 |
| 14 | 133.43 | CH | 5.78,dd,15,11 | H-3,H-15,H-16 |
| 15 | 132.16 | CH | 5.91,appt,13 | H-13,H-14,H-17 |
| 16 | 129.29 | CH | 5.55,dq,13,7 | H-14,H-17 |
| 17 | 18.15 | CH₃ | 1.66,d,7 | H-15,H-16 |
| 18 | 22.53 | CH₃ | 1.55,appt,1.5 | H-3,H-5 |
| 19 | 22.75 | CH₃ | 0.90,d,6.5 | H-7 |
| 2' | 178.02 | C° | — | H-5',H-7' |
| 3' | 101.60 | C° | — | — |
| 4' | 191.54 | C° | — | H-5',H-6' |
| 5' | 68.79 | CH | 3.60,t,2.5 | H-61,H-7' |
| 6' | 59.62 | CH₂ | 3.87,dd,12,3 3.80,dd,12,3 | H-51 |
| 7' | 27.45 | CH₃ | 2.97,brs | — |
| C-10H | — | — | 17.42,brs | — |

Hydrogenation of Compound B (to give Compound C):

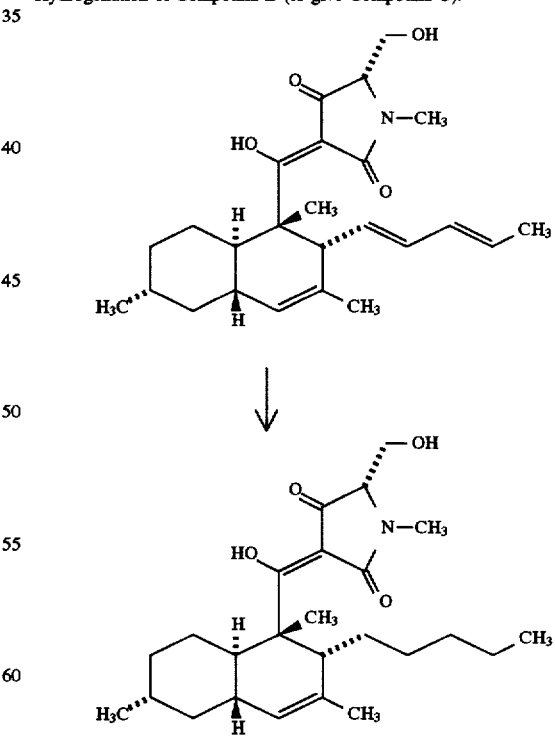

To a solution of Compound B (5 mg) in ethyl acetate (0.7 mL) and methanol (0.3 mL) was added 5% Pd/C and the mixture was hydrogenated at ambient pressure overnight. The progress of the reaction was monitored by analytical HPLC, reverse-phase C-8 silica gel; 4.6×250 mm; 80% aqueous acetonitrile containing 0.1% TFA; 1 mL per min). After completion of the reaction, the catalyst was removed by filtration through Celite and the filtrate was was concentrated to dryness and chromatographed over a reverse-phase C-8 silica gel (9.4×250 mm) HPLC column. The column was eluted with a 60 min gradient of 60% to 80% aqueous acetonitrile containing 0.1% TFA at a flow rate of 4 mL per min. The product was eluted between 33–34 min. Lyophilization of the fractions afforded 3 mg of the tetrahydro product Compound C as an amorphous powder. HREIMS (m/z): 417.2837 (0.1%, M+, calcd. for $C_{25}H_{39}O_4N$: 417.2879), 399.2768 (6.3%, calcd. for $C_{25}H_{37}O_3N$: 399.2773), 247.2419 (94%, calcd. for $C_{18}H_{31}$: 247.2426), 187.1478 (80%, calcd. for $C_{14}H_{19}$: 187.1487), 177.1635 (16%, calcd. for $C_{13}H_{21}$: 177.1643), 170.0490 (7%, calcd. for $C_7H_8O4N$: 170.0453). $^1H$ NMR ($CDCl_3$, Only distinguishable shifts are listed): 0.80 (3H, t, J=6.8 Hz, $CH_3$), 0.91 (3H, d, J=6.4 Hz, $CH_3$), 1.37 (3H, s, $CH_3$), 1.71 (3H, s, $CH_3$), 3.07 (3H, s, $NCH_3$), 3.63 (1H, t, J=4.4 Hz,H-5'), 3.88 (1H, dd, J =11.6, 5.2 Hz, H-6'), 4.04 (1H, dd, J=11.2,4.0 Hz, H-6'), 5.09 (1H, brs, H-5).

EXAMPLE 8

Assay for Inhibition of Strand Transfer by HIV Integrase

Inhibition of strand transfer was conducted according to Hazuda, D. J. et al. Nucleic Acids Res., 22, 1121 (1994), hereby incorporated by reference for these purposes.

Results of the assay follow:

| Compound | IC$_{50}$ |
|---|---|
| A | 7 μm |
| B | 11 μm |
| C | 5 μm |

While the foregoing specification teaches the principles of the present invention, with examples provided for the purpose of illustration, it will be understood that the practice of the invention encompasses all of the usual variations, adoptions, or modifications, as come within the scope of the following claims and its equivalents.

What is claimed:

1. A compound of the formula

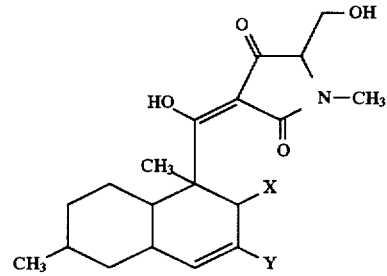

wherein X is

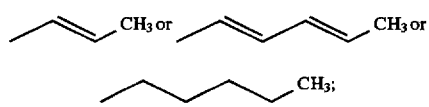

Y is H or $CH_3$, or pharmaceutically acceptable salts thereof, with the proviso that the compound is not 2. A compound according to claim 1 of the formula:

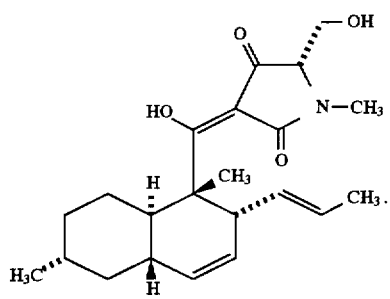

wherein X is

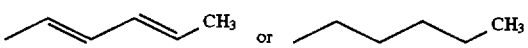

and Y is H or $CH_3$, or a pharmaceutically acceptable salt thereof.

3. A compound according to claim 1 or 2 which is:

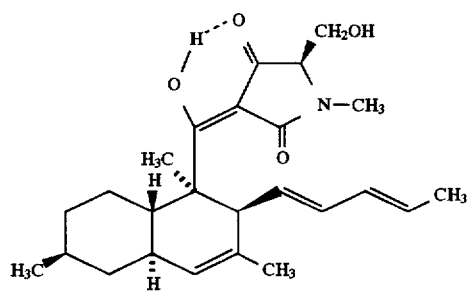

or a pharmaceutically acceptable salt thereof.

4. The compound according to claim 1 or 2 which is:

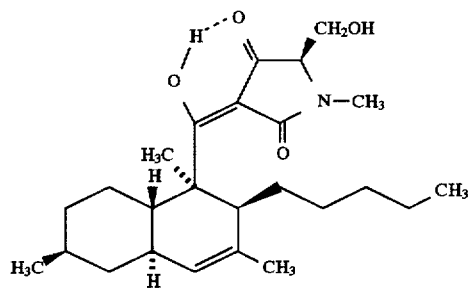

or a pharmaceutically acceptable salt thereof.

* * * * *